United States Patent
Arbas

(10) Patent No.: US 10,383,563 B2
(45) Date of Patent: *Aug. 20, 2019

(54) SYSTEM AND METHOD TO DETECT ALERTNESS OF MACHINE OPERATOR

(71) Applicant: J. Kimo Arbas, Los Angeles, CA (US)

(72) Inventor: J. Kimo Arbas, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/583,474

(22) Filed: May 1, 2017

(65) Prior Publication Data

US 2017/0231546 A1    Aug. 17, 2017

Related U.S. Application Data

(63) Continuation of application No. 14/660,155, filed on Mar. 17, 2015, now Pat. No. 9,636,063.
(Continued)

(51) Int. Cl.
| | |
|---|---|
| *A61B 5/18* | (2006.01) |
| *A61B 5/0476* | (2006.01) |
| *A61B 5/11* | (2006.01) |
| *A61B 5/0488* | (2006.01) |
| *A61B 5/0205* | (2006.01) |

(Continued)

(52) U.S. Cl.
CPC .............. *A61B 5/18* (2013.01); *A61B 5/0205* (2013.01); *A61B 5/0476* (2013.01); *A61B 5/0488* (2013.01); *A61B 5/082* (2013.01); *A61B 5/11* (2013.01); *A61B 5/165* (2013.01); *A61B 5/4806* (2013.01); *A61B 5/4845* (2013.01); *A61B 5/6803* (2013.01); *A61B 5/7264* (2013.01); *A61B 5/742* (2013.01); *A61B 5/7405* (2013.01); *A61B 5/746* (2013.01); *A61B 5/7455* (2013.01); *A61B 5/024* (2013.01); *A61B 5/4809* (2013.01); *A61B 2560/0242* (2013.01); *A61B 2562/0219* (2013.01)

(58) Field of Classification Search
CPC ........... A61B 5/18; A61B 5/0476; A61B 5/11; A61B 2017/00216; A61B 5/0488; A61B 5/0205; A61B 5/165; A61B 5/4809; A61B 5/4845; A61B 5/6803; A61B 5/7264; A61B 5/746; A61B 5/024
See application file for complete search history.

(56) References Cited

U.S. PATENT DOCUMENTS

| | | | |
|---|---|---|---|
| 2002/0171551 A1 | 11/2002 | Eshelman et al. | |
| 2004/0030531 A1* | 2/2004 | Miller ................ | A61B 5/0002 702/182 |

(Continued)

OTHER PUBLICATIONS

NeuroSky, "MindWave Mobile: MyndPlay Bundle", http://store.neurosky.com/products/mindwave-mobile, retrieved from the internet on Mar. 27, 2015, 4 pages.

*Primary Examiner* — Alyssa M Alter
(74) *Attorney, Agent, or Firm* — Fish & Richardson P.C.

(57) ABSTRACT

A system and method relate to receiving, by a processing device, at least one stream of data captured by at least one sensor monitoring a human subject, wherein the at least one stream of data comprises sensor measurements, comparing the sensor measurements to at least one model of a mental state to estimate the mental state of the human subject, determining whether to trigger an alarm based on the estimated mental state, and in response to determining to trigger the alarm, generating an instruction to trigger the alarm.

6 Claims, 6 Drawing Sheets

Related U.S. Application Data

(60) Provisional application No. 61/954,819, filed on Mar. 18, 2014.

(51) Int. Cl.
   *A61B 5/16* (2006.01)
   *A61B 5/00* (2006.01)
   *A61B 5/08* (2006.01)
   *A61B 5/024* (2006.01)

(56) References Cited

U.S. PATENT DOCUMENTS

| | | | | |
|---|---|---|---|---|
| 2008/0027337 A1* | 1/2008 | Dugan | ............... | A61B 5/0002 600/508 |
| 2009/0312817 A1* | 12/2009 | Hogle | ............... | A61B 5/0492 607/54 |
| 2015/0031964 A1* | 1/2015 | Bly | ............... | A61B 5/165 600/301 |
| 2015/0164351 A1* | 6/2015 | He | ............... | A61B 5/1171 702/19 |
| 2015/0199010 A1 | 7/2015 | Coleman et al. | | |

\* cited by examiner

SYSTEM AND METHOD TO DETECT ALERTNESS OF MACHINE OPERATOR

RELATED APPLICATION

The present application is a continuation of and claims the benefit of priority to U.S. Pat. No. 9,636,063, issued on May 2, 2017, which claims the benefit of U.S. Provisional Patent Application No. 61/954,819, filed Mar. 18, 2014, the content of which is hereby incorporated by reference.

TECHNICAL FIELD

This disclosure relates to detecting mental states of human subjects, in particular, to detecting the alertness of machine operators.

BACKGROUND

Human operators often operate heavy machines. To safely operate these machines, human operators need to be mentally alert and focused. However, many factors may cause the machine operators to lose their mental alertness and focus while operating the heavy machines, thereby creating hazard or even deadly situations. For example, operators of transportation vehicles such as automobiles, trucks, trains, airplanes, and ships may doze off due to fatigue or sleep deprivation, thereby creating dangerous situations to the surroundings. In fact, many major accidents occur because operators of transportation vehicles fell asleep during work. Further, operators of transportation vehicles sometimes may also operate under chemical influences. For example, a driver of a vehicle may drive under the influence of alcohol or drugs. In these situations, the operators may also lose his or her mental sharpness and focus, thereby creating dangerous situations.

SUMMARY

The following is a simplified summary of the disclosure in order to provide a basic understanding of some aspects of the disclosure. This summary is not an extensive overview of the disclosure. It is intended to neither identify key or critical elements of the disclosure, nor delineate any scope of the particular implementations of the disclosure or any scope of the claims. Its sole purpose is to present some concepts of the disclosure in a simplified form as a prelude to the more detailed description that is presented later.

Implementations of the disclosure may relate receiving, by a processing device, at least one stream of data captured by at least one sensor monitoring a human subject, wherein the at least one stream of data comprises sensor measurements, comparing the sensor measurements to at least one model of a mental state to estimate the mental state of the human subject, determining whether to trigger an alarm based on the estimated mental state, and in response to determining to trigger the alarm, generating an instruction to trigger the alarm.

Implementations of the disclosure may include a wearable device including an electroencephalography (EEG) sensor to detect a brain wave data of a human subject, a heart rate sensor to detect a heart rate data of the human subject, an electromyography (EMG) sensor to detect an electrical activity data relating to eye blinks by the human subject, an accelerometer to detect an acceleration data of the human subject, and a warning device to generate an alarm in response to identifying occurrence of a mental state of the human subject based on at least one of the brain wave data, the heart rate data, the electrical activity data, or the acceleration data.

BRIEF DESCRIPTION OF THE DRAWINGS

The present disclosure is illustrated by way of example, and not by way of limitation, in the figures of the accompanying drawings.

DETAILED DESCRIPTION

Implementation of the present disclosure may include a system and method to determine mental states of human subjects such as, for example, machine operators. The system may include multiple sensors that may collect physical and physiological measurements relating to the mental states of the machine operator. These sensors may further include analog-to-digital converters (ADCs) that may convert the measurements into digital signals. Further, these sensors may be operatively coupled to a processing device (such as a central processing unit (CPU)) to analyze the digital signals and determine the mental states of the machine operator based on the analysis. In the event that the processing device determines that the mental state of the operator is below a predetermined level of competence or otherwise violates a mental state criterion, the processing device may cause an alarm transmitter to send out an alarm signal over a transmission network. In one implementation, the alarm signal may include a warning to the operator to wake up the operator. Alternatively, the transmitter may send the alarm to a central monitor who may then inform an authority or the operator.

In one implementation, the system may continuously monitor the mental state of machine operators and send out alarms in response to detecting incapacity by the operators so that accidents may be prevented from happening.

Figure 1:
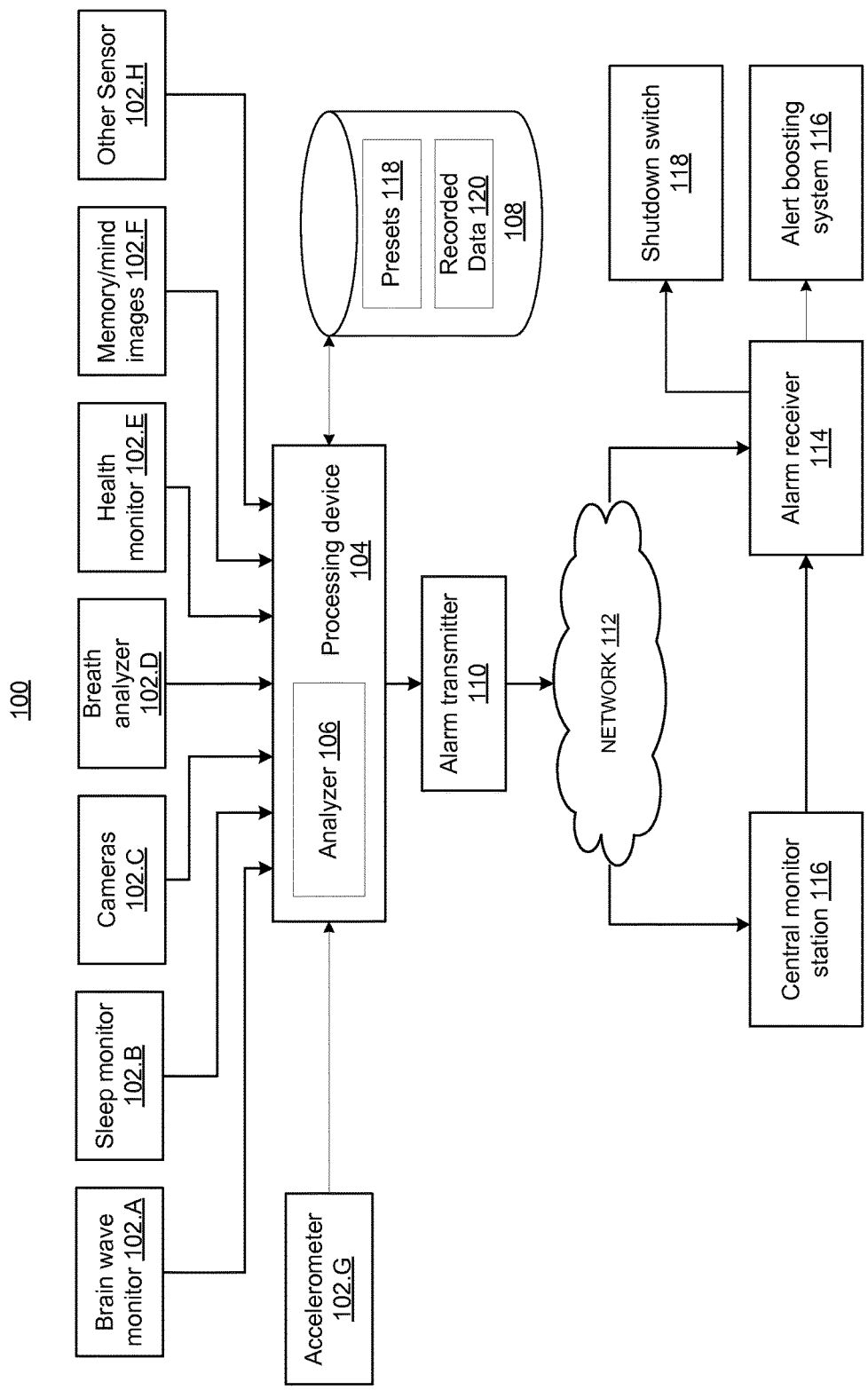
FIG. 1 illustrates a system architecture in which aspects of the present disclosure can be implemented.

FIG. 1 illustrates a system 100 to determine the mental state of an operator and transmit an alarm in the event of detecting mental incompetence or an impaired mental state of the operator according to implementations of the present disclosure. Referring to FIG. 1, system 100 may include a number of sensors 102.A-102.H. Each of the sensors may measure physical and/or physiological responses from a human subject such as a machine operator. The measured quantities may be directly and indirectly related to the mental states of the human operator.

In one implementation, sensors 102.A-102.G may be analog sensors, e.g., those that record the measured quantities continuously over time. In another implementation, sensors 102.A-102.G may be digital sensors that record samples of the measured quantities according to a sampling frequency (e.g., at 30 data samples per second). In one implementation, each of the analog sensors may include an analog-to-digital converter (ADC) (not shown) that may sample and digitize the measured analog quantities and convert them into digital quantities. Thus, for the convenience of discussion, the outputs of sensors 102.A-102.G may be considered to be streams of data samples, where each stream corresponds to a specific measurement from one of the sensors 102.A through 102.H.

The sensors may include a brain wave monitor 102.A. Sensors may additionally include one or more of a sleep monitor 102.B, one or more cameras 102.C, a breath analyzer 102.D, a health analyzer 102.E, one or more mind imagers 102.F, an accelerometer, and/or other sensors 102.H. Other sensors may include an environmental sensor such as a temperature sensor, and so forth.

The outputs of sensors 102.A-102.H may be communicatively coupled to a processing device 104 that may be a central processing unit (CPU) including one or more processing cores (not shown) that may receive the data streams from sensors 102.A-102.H. Processing device 104 may be coupled to a storage device 108 (such as a memory device or a hard drive) to store parameterized models of mental states of human subjects that are also referred to as presets 118, and the received streams of data samples as recorded data 120. These presets 118 may model different kinds of mental states such as alert, unfocused, and drowsy etc. Implementations of the present disclosure may detect various mental states or symptoms including drowsiness, intoxication, confusion, stress, rage, anxiety, and distractedness. Implementations may further detect mental states relating to health emergencies or impending health issues including, but not limited to, unconsciousness, alertness (or lack alertness), focus (or lack of focus), meditative mental states, anger, joy, depression.

Further, processing device 104 may execute instructions of an analyzing software application ("analyzer") 106 to analyze the measured quantities received from sensors 102.A-102.H, compare the received quantities with the stored parameterized models of mental states, and determine the mental state of the machine operator. In the event that processing device 104 determines that the present mental state of machine operator is not suited to operate the machine, processing device 104 may generate an alarm signal at an output of the processing device 104 and transmit the alarm signal to an alarm.

The output of processing device 104 may be coupled to an alarm transmitter 110. In one implementation, alarm transmitter 110 may be a broadcasting device that may broadcast the alarm to a network 112. Network 112 may be any type of network infrastructures that are suitable to reliably transmit the alarm signal to destination device. In one implementation, network 112 may be a wired communication network such as an Internet protocol (IP) based communication network. In another implementation, network 112 may be a wireless network that may transmit the alarm signal over the air to destination devices. Under both the wired and wireless networks 110, the alarm transmitter may transmit the alarm signal over network 112 as data packets that each may include an identifier to identify the payload of the packets as containing an alarm signal.

Alarm transmitter 110 may broadcast the alarm signal over network 112 to different destination devices. In one implementation, alarm signal may be transmitted to a central monitor station 116 where the detected mental state of the machine operator may be verified by a monitor. If the mental state of the machine operator is determined unfit to continue operating the machine, central monitor station 116 may transmit the alarm to an alarm receiver 114 which may convert the alarm signal into a warning to warn the machine operator. For example, in one implementation, alarm receiver 114 may, in response to receiving the alarm signal, send out an audio message to the machine operator to remind him or her to pay attention.

In another implementation, alarm transmitter 110 may transmit the alarm signal directly to alarm receiver 114 bypassing central monitoring station 116. Although under this scenario, the alarm signal is not verified by a central monitor station before transmitting to alarm receiver 114, the alarm signal may be transmitted to the machine operator directly without further delay.

Sensors 102.A-102.H may measure different physical and physiological responses from the machine operators. These sensors may be either intrusive or non-intrusive. Intrusive sensors may attach a sensing device on the machine operator so that the machine operator may be consciously aware of the existence of the sensing device, while non-intrusive sensors may be placed discreetly in a place that is away from the machine operator so that the machine operator is not consciously aware of the existence of the sensing device. Intrusive sensors may capture measurement data with less noise because of the proximity between the sensing device and the machine operator, while non-intrusive sensors do not interfere with the machine operator.

In one implementation, the sensors of system 100 may include a brain wave monitor 102.A to measure brain (or mind) activities of the machine operator. In one implementation, brain wave monitor 102.A may be an electroencephalography (EEG) monitor that may record electrical activity data along the scalp surface of the machine operator. The EEG monitor may include an array of electrodes that may measure voltage fluctuations resulting from ionic current flows within the neurons of the brains. The instantaneous voltage potentials captured at these electrodes may be recorded in a memory coupled to the EEG monitor. In one implementation, the EEG monitor may be a mobile EEG monitor (such as a Neurosky® MindWave Mobile sensor). The mobile EEG monitor may be a headset that may be mounted on the head of the machine operator. The mobile EEG monitor may include multiple electrode sensors that may record voltage potentials on multiple scalp locations. Further, the mobile EEG monitor may include hardware processor (such as a digital signal processor (DSP)) that may record voltage potentials detected at these scalp locations (raw signals) and compute frequency spectrums of the raw EEG signals. In one implementation, the hardware processor of the mobile EEG monitor may further include meters for attention and blink detection derived from the raw EEG signals and their corresponding spectrum. The mobile EEG monitor may include a wireless transmitter that may transmit the recorded raw data, their spectrum data, and the derived attention and blink to the processing device 104 over a wireless transmission channel such as Bluetooth® technology.

Figure 2A:
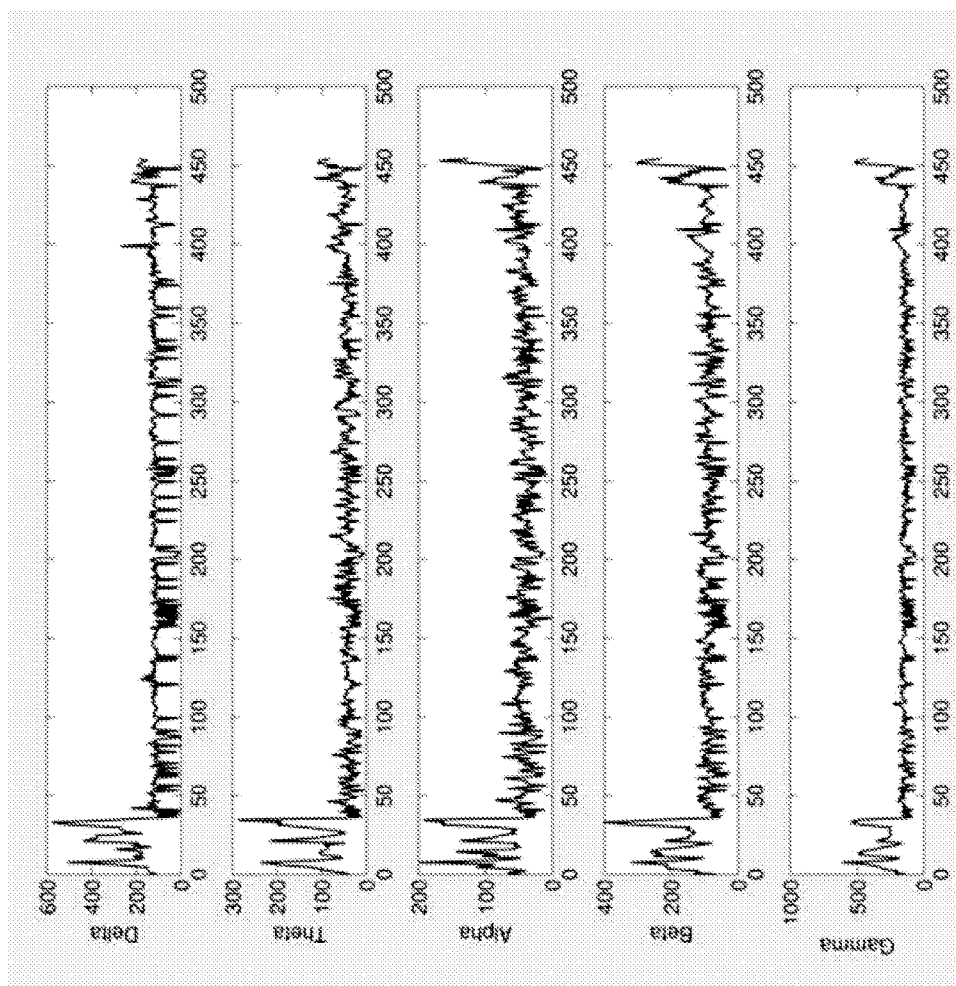
FIG. 2A illustrates exemplary raw data recorded at a number of electroencephalography (EEG) electrodes according to some implementations of the present disclosure.
Figure 2B:
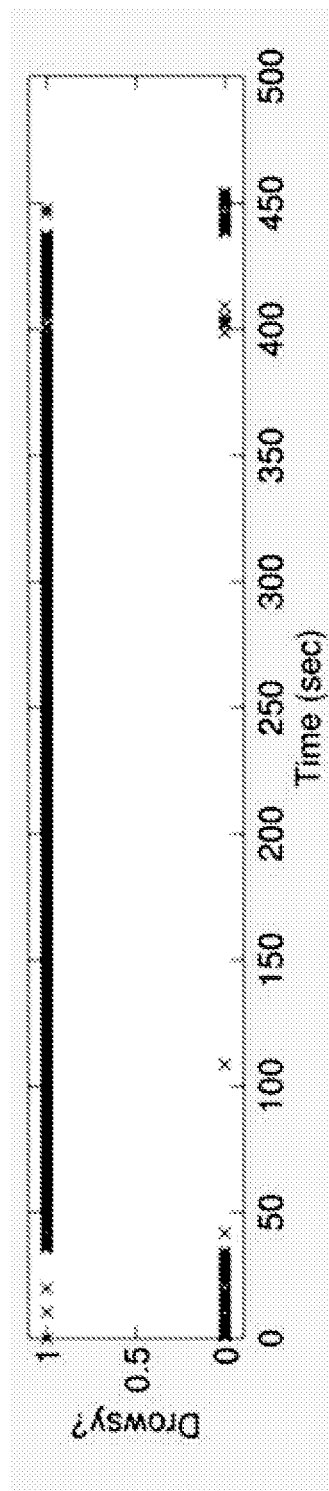
FIG. 2B illustrates an exemplary EEG brain wave pattern that shows little electrical activities according to an implementation of the present disclosure.

In one implementation, the recorded raw data may include multiple channels. Each of the channels may record the raw data for a specific frequency range (e.g., Delta, Theta, Alpha, Beta, Gamma ranges). FIG. 2A illustrates exemplary raw data recorded by an EEG electrode according to some implementations of the present disclosure. As shown in FIG. 2A, for example, five EEG data in frequency ranges (Delta, Theta, Alpha, Beta, Gamma) may be captured by one EEG electrode. In particular, the EEG electrode measures voltage fluctuations resulting from ionic current flows within the neurons of the brain. The measured EEG raw data indicate the brain's spontaneous electrical activities over time. Thus, FIG. 2A illustrates the spontaneous electrical activities measured at the electrode location. When the machine operator is mentally alert and his or her brain functions actively, the brain wave, as shown in FIG. 2A, may include activity events. If, however, the machine operator loses his or her mental alertness due to drowsiness, the brain wave may include little or no activities. FIG. 2B illustrates an exemplary EEG brain wave pattern that shows little electrical activities. In one implementation, the brain electrical activities of a well-rested, alert person may be recorded the preset 118 and stored in the data storage 108 as shown in FIG. 1. The brain wave of the machine operator while working may be captured and compared with the preset to determine whether the machine operator is falling into asleep. In one implementation, the processing device 104 may use the received raw signals, spectrum, and derived attention and eye blinks as part of the factors in determining the mental states of the machine operator. These factors may be fed into the analyzer 106 to detect the mental state of the machine operator.

In one implementation, the EEG monitor may output streams of data samples (including raw signals and spectrum) at a higher sampling rate (e.g., 512 Hz), while the computation output (including attention and eye blink) at a lower sampling rate (e.g., at 1 Hz). Thus, the detected attention and eye blink of the machine operator may be transmitted to the processing device 104 at lower rate (e.g., one frame per second) while the raw signals and the spectrum are generated at a much higher rate (e.g., 512 frames per second).

In one implementation, sensors of system 100 may include a sleep monitor 102.B to measure quality of sleep and amount of sleep. For example, wearable sensors (such as Fitbit™ types of sensors) may monitor the machine operator during his or her sleep to determine the level of sleep. The monitored factors may include body movement during sleep (e.g., how often the person gets up or moves around), blinking or open eyes during sleep, heartbeat, and blood pressure, and factors empirically-known related to good or bad sleep. In one implementation, the sleep monitor 102.B may measure the quality and amount of sleep and quantify the quality and amount of sleep in numerical scales. For example, the quality of sleep and amount of sleep each may be quantified in a scale from 1 to 10 with 10 as the highest quality and sufficient amount (e.g., greater than seven hours) of sleep and 1 as the lowest quality and the critically low amount (e.g., below a threshold such as four hours) of sleep. In one implementation, the sleep monitor 102.B may include a wireless transmitter that may transmit the numerical values of the quantifications of sleep quality and amount to the processing device 104 over a wireless communication channel. The processing device 104 may use the received values of sleep quality and amount as part of the factors in determining the mental states of the machine operator.

In one implementation, the sleep monitor 102.B may include an electromyography (EMG)-based blink detection system. The EMG sensor may detect and record the electrical activities by the skeletal muscles such as, for example, the electrical activities generated by eye blinks. The detected EMG signals may be transmitted to the processing device 104 that may execute the analyzer 106 to determine an eye blink rate of the machine operator while operating the machine. In one implementation, the analyzer 106 may analyze the received EMG signal and determine an eye blink rate. Further, the analyzer 106 may determine whether the machine operator is falling into sleep based on the eye blink rate. For example, an abnormal high eye blink rate may indicate that the operator is about to falling into sleep.

In one implementation, sensors of system 100 may include a camera 102.C to monitor the eye movement and perform face recognition. Camera 102.C may include a suitable imaging sensor that may optically record the facial region and surrounding environment of the machine operator. Types of camera 102.C may include, but not limited to, charge-coupled device (CCD) cameras, complementary metal-oxide semiconductor (CMOS) cameras, infrared cameras, video cameras, and digital/analog cameras. In one implementation, camera 102.C may capture stack of image frames at a fixed frequency (e.g., 30 frames per second), each image frame including a two-dimensional array of pixel values. In one implementation, camera 102.C may be a color camera, each pixel including three intensity values (e.g., intensities for Red, Green, Blue channels). In another implementation, camera 102.C may be a black and white camera, each pixel including only one greyscale value. Camera 102.C may constitute a non-intrusive sensor that may be mounted on a platform to passively monitor the face image of the machine operator. In one implementation, camera 102.C may stream the captured image frames to processing device 104 over a communication link (e.g., a wideband communication channel). Processing device 104 may receive these image frames and derive eye movement, face recognition, mood recognition, and detections of distraction, intent, and concealed intent of the machine operator. In one implementation, off-the-shelve face detection, eye movement detection, emotion recognition, and distraction detection software applications may be used to detect these factors.

In one implementation, sensors of system 100 may include a breath analyzer 102.D to continuously or periodically monitor the breath of the machine operator. The breath analyzer may include chemical testers that may react to alcohol and/or drug contents in the breath of the machine operator if there is any. In the event that alcohol and/or contents are detected in the breath, the breath analyzer may transmit a level of the contents detected in the breath to processing device 104 which may take the level into consideration in determining the mental state of the machine operator.

In one implementation, sensors of system 100 may include a health monitor 102.E to continuously or periodically monitor the health of the machine operator. In one implementation, the health monitor 102.E may monitor vital signs of the machine operator, including body temperature, heart rate, blood pressure, sweating, and physical and chemical characteristics of blood (e.g., blood oxygen level), etc. Based on these vital signs, the health monitor may compute indicators for hypertension, stroke, malnourishment, dehydration, heart attack, heart palpitations, fatigue, psychological or psychiatric imbalance/abnormality, lack of vital fluids (e.g., blood), and psychosis etc. In one implementation, a heart rate sensor may be used to detect the heart rate of the machine operator. The detected heart rate may be an indicator of whether the machine operator is under the influence of alcohol or narcotics. For example, the heart rate of a truck driver should be consistently within a range of his or her normal heart rate (e.g., 60 to 80 beats per minute). When the truck driver's heart rate is increased to an elevated level compared to his or her normal range over a predetermined period of time, the truck driver may be driving under influence. For example, the heart rate sensor may detect that the truck driver may have a heart rate in a range that is 30% higher than the normal range for more than five minutes. This information may be transmitted from the heart rate sensor over a communication link (e.g., a wireless link) to the processing device 104 that may execute the analyzer 106 to determine whether the truck driver is driving under the influence of narcotics.

In one implementation, the heart rate sensor may be a wristband or armband that the machine operator wears on his or her wrist or arm. For example, the machine operator may wear a Polar® heart rate monitor with Bluetooth® connection. In another implementation, the heart rate sensor may be part of a headband integrated with the brain wave monitor 102.A. The integrated head band monitor may have the advantage that the machine operator wears one device that can record multiple vital signals.

In one implementation, sensors of system 100 may include a memory and mind image monitor 102.F to monitor memory, mind image, and/or thoughts. The mind images are images subjectively seen in the mind of the machine operator, consciously or subconsciously, and the dialog or monologue of consciousness (or talking to oneself in the mind).

Figure 2C:
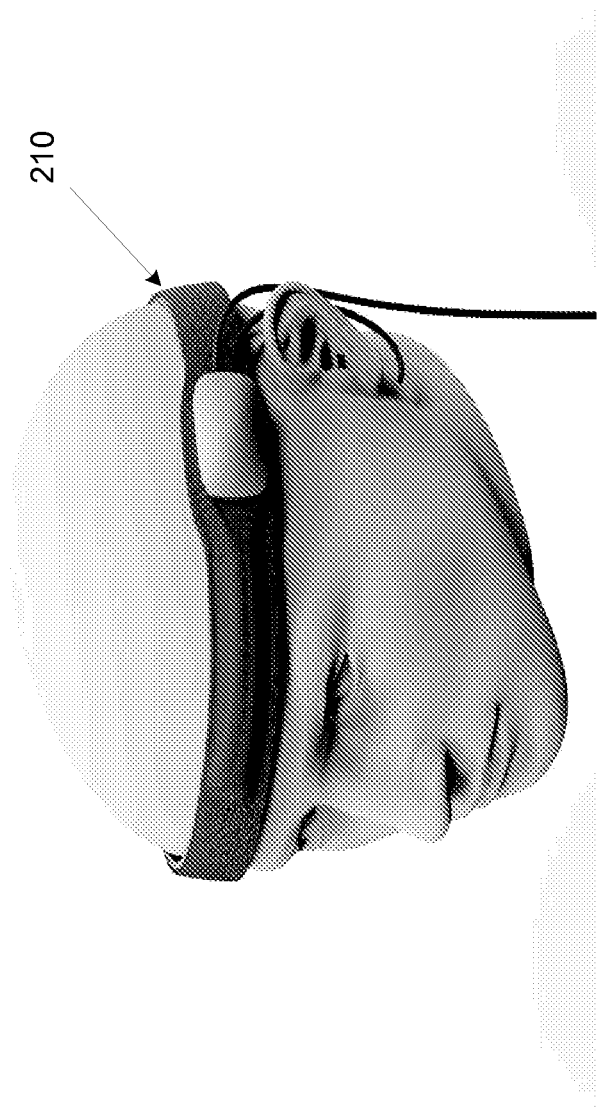
FIG. 2C illustrates a head mounted device according to an implementation of the present disclosure.

In one implementation, system 100 may further include an accelerometer 102.G embedded in a headset (e.g., the headband as shown in FIG. 2C). The accelerometer 102.G embedded in a headset is a device that may measure the proper acceleration of the head. For example, when the machine operator is in a drowsy state, he or she may suffer micro sleeps that may last a fraction of a second to more than one second. During micro sleeps, the machine operator may involuntarily nod his or her head (i.e., accelerations) with sudden head lifts (i.e., decelerations). The accelerometer 102 may measure and record the acceleration signals, and further transmit the acceleration (or deceleration) signals, via a Bluetooth link, to the processing device 104 that may execute the analyzer 106 to determine micro sleep episodes based on the detected head nods by the machine operator.

In one implementation, system 100 may include other types of sensors that may provide useful information to determine the mental state of the machine operator. For example, sensors 102.H may include environmental sensors to detect atmospheric data, environmental temperatures, oxygen levels, and atmospheric pressures.

In one implementation, sensors 102.A through 102.H may be wearable sensors that the machine operator may wear on his/her body. Further, sensors 102.A through 102.H may be mobile sensors that are communicatively coupled to processing device 104 through wireless communication links.

The processing device 104 may receive data from one or more sensors 102.A through 102.H and perform analysis on the received data. In one implementation, processing device 104 may store the received data in a storage device 108 as the recorded data 120. In one implementation, the storage device 108 may be a local storage to the processing device 104 so that recorded data 120 may be retrieved by the processing device 104 quickly. In another implementation, the storage device may be coupled to the processing device 104 remotely through a communication network 112. For example, storage device 108 may be in the cloud managed by a third party. The data stored in the cloud may be retrieved by the processing device 104 through the communication network (such as the Internet).

In one implementation, as shown in FIG. 2C, one or more sensors 102.A-102.H and an alarming device may be integrated into a headband 210. The machine operator may be required to wear the headband 210 during the operation of the machine (e.g., driving a truck). In one implementation, the headband may include a brain wave sensor (EEG), a heart rate monitor, an electromyography (EMG) sensor, and/or an accelerometer. These sensors may measure brain waves, heart rates, electrical activities by eye blinks, and accelerations caused by head nods. The headband 210 may further include a communication device that may transmit the data collected by these sensors to the processing device 104 and receive instructions from the processing device 104. In one implementation, the headband 210 may include a warning device such as, for example, an alarm sound generator and/or a vibration generator. The processing device 104 may analyze sensor data received from the headband 210 and determine that the machine operator is in a mental state (e.g., drowsy) that is dangerous to continue operation and needs to be warned. The processing device 104 may transmit an instruction to the communication device on the headband 210. The communication device may further transmit the instruction to the warning device that may generate an alarm to the machine operator. For example, in response to receiving an instruction because of the drowsiness of a truck driver, the warning device may generate sound (e.g., music or ring tone) and/or vibration to wake up the driver.

Models of mental states may also be stored on the storage device 108. The mental states may be a parameterized model that may be described using a set of parameters (referred hereinafter as presets 118). In one implementation, presets 118 may include a set of threshold values that may define different mental states including, for example, an alertness state, a drowsiness state, a sleep state, and an intoxication state. Other mental states include a rage state, a depression state, and a meditative state. These mental states may be detected by machine learning approaches based on empirical data of one or more the data received from sensors 102.A-102.H. For example, the support vector machine (SVM) may be used to determine these mental states.

Figure 3:
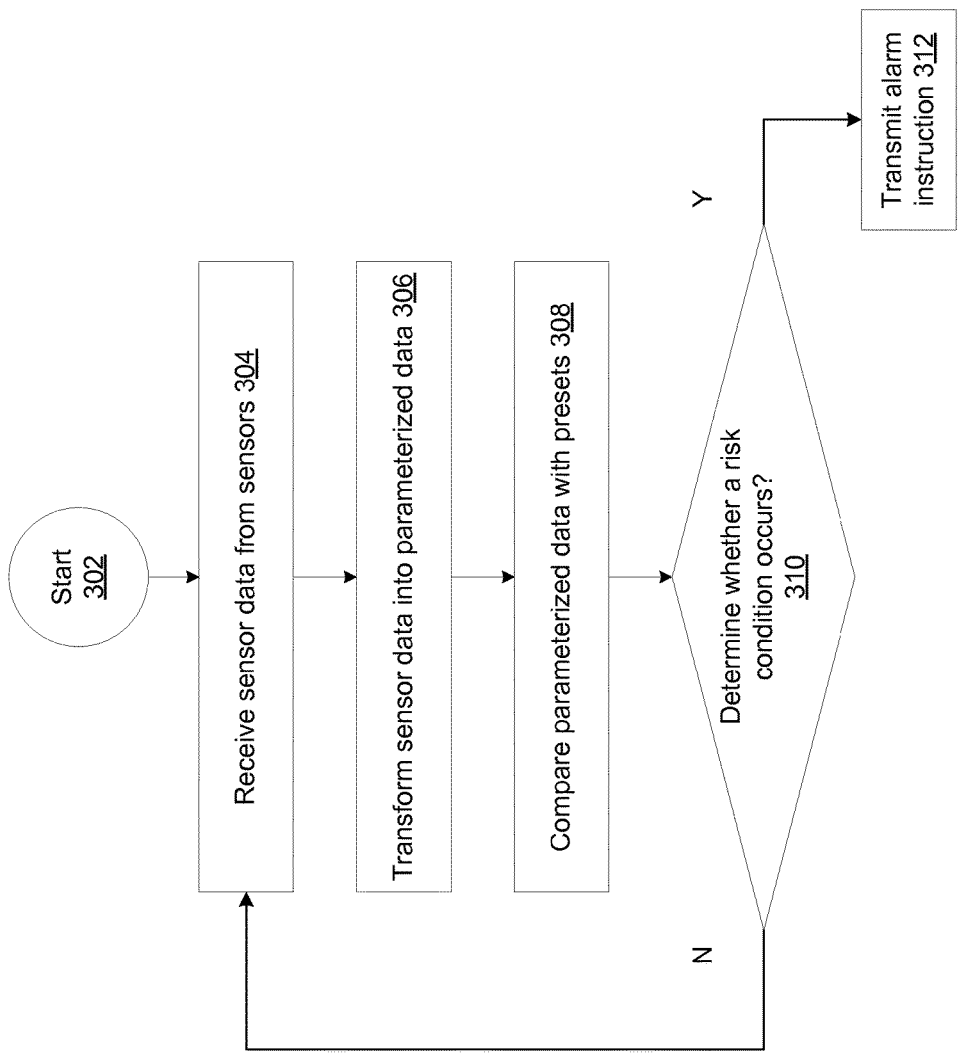
FIG. 3 illustrates a flow diagram of a method to determining a mental state of a human subject according to an implementation of the present disclosure.

In one implementation, processing device 104 may execute an analyzing module ("analyzer") 106 to determine the mental state of the machine operator in real time. FIG. 3 illustrates a flow diagram of a method 300 to determine the mental state of the machine operator according to implementations of the disclosure. The method may be performed by processing logic that comprises hardware (e.g., circuitry, dedicated logic, programmable logic, microcode, etc.), software (e.g., instructions run on a processing device to perform hardware simulation), or a combination thereof.

For simplicity of explanation, the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events. Additionally, it should be appreciated that the methods disclosed in this specification are capable of being stored on an article of manufacture to facilitate transporting and transferring such methods to computing devices. The term "article of manufacture," as used herein, is intended to encompass a computer program accessible from any computer-readable device or storage media. In one implementation, the methods may be performed by the analyzer 106 as shown in FIG. 1.

Referring to FIG. 3, at 302, the processing device 104 may start to execute analyzer 106 to determine the mental state of a machine operator. In one implementation, the analyzer 106 may be started in response to the machine operator turns on the ignition of the machine such as starting a vehicle. At 304, the processing device 104 may receive streams of data samples captured by one or more of sensors 102.A through 102H. As discussed above, the captured data may include raw EEG signals and their spectrum data, attention and eye blinks derived from an EMG sensor signals and their spectrum, numerical values of quality and amount of sleeps, image frames that capture the face images of the machine operator, alcohol content data, health data, and environmental data. Received data may also include motion data of the machine operator.

At 306, processing device 104 may transform the received data into a parametric space according to which the mental states have been modeled. The transformation may be a linear transformation, or alternatively, non-linear transformation into parameterized data. At 308, processing device 104 may retrieve presets from the storage device and compare the parameterized data with the presets to determine the mental states of the machine operator. At 310, processing device 104 may determine whether the mental state of the machine operator causes a risky situation. In response to determining that the mental state of the machine operator is not at risk, the processing device 104 may repeat the process by going back to 304 to receive further data from sensors. However, if it is determined that the mental state of the machine operator is not suitable to operate the machine, at 312, the processing device 104 may generate an instruction to the alarm transmitter to instruct a warning device to generate an alarm.

In the event that an alarm instruction is sent to the alarm receiver 114, the alarm receiver 114 may cause an alertness boosting system 116 to activate. The alertness boosting system 116 may be a device that could be activated to boost the alertness of the machine operator. In one implementation, in response to the received alarm, the alert boosting system may cause light effects to show to the operator. For example, fading/increasing light, flashing lights, or turning on light towards the machine operator may be used to boost his/her alertness. In one implementation, the machine operator's alertness is boosted by turning on or changing the light color to blue. In other implementations, the alertness boosting system may generate sound (e.g., loud music), vibrate the seat on which the machine operator sits, vibrate a headband that the operator wears, and change the room temperature (e.g., injecting cold air through air conditioner) to boost the alertness of the machine operator. In one implementation, the alertness boosting system may inject Adrenalin boosters such as, for example, caffeine, into the body of the machine operator.

In one implementation, in response to a determination that the machine operator is totally incapacitated (e.g., falling into sleep), the alarm receiver 114 may activate a shutdown switch 118 to initiate a shutdown process. The alarm receiver 114 may also be capable of informing the mental state to a third party such as a supervisor, a copilot, a designated team member, a family member, an emergency contact, and a medical staff etc.

In the foregoing description, numerous details are set forth. It will be apparent, however, to one of ordinary skill in the art having the benefit of this disclosure, that the present disclosure may be practiced without these specific details. In some instances, well-known structures and devices are shown in block diagram form, rather than in detail, in order to avoid obscuring the present disclosure.

Figure 4:
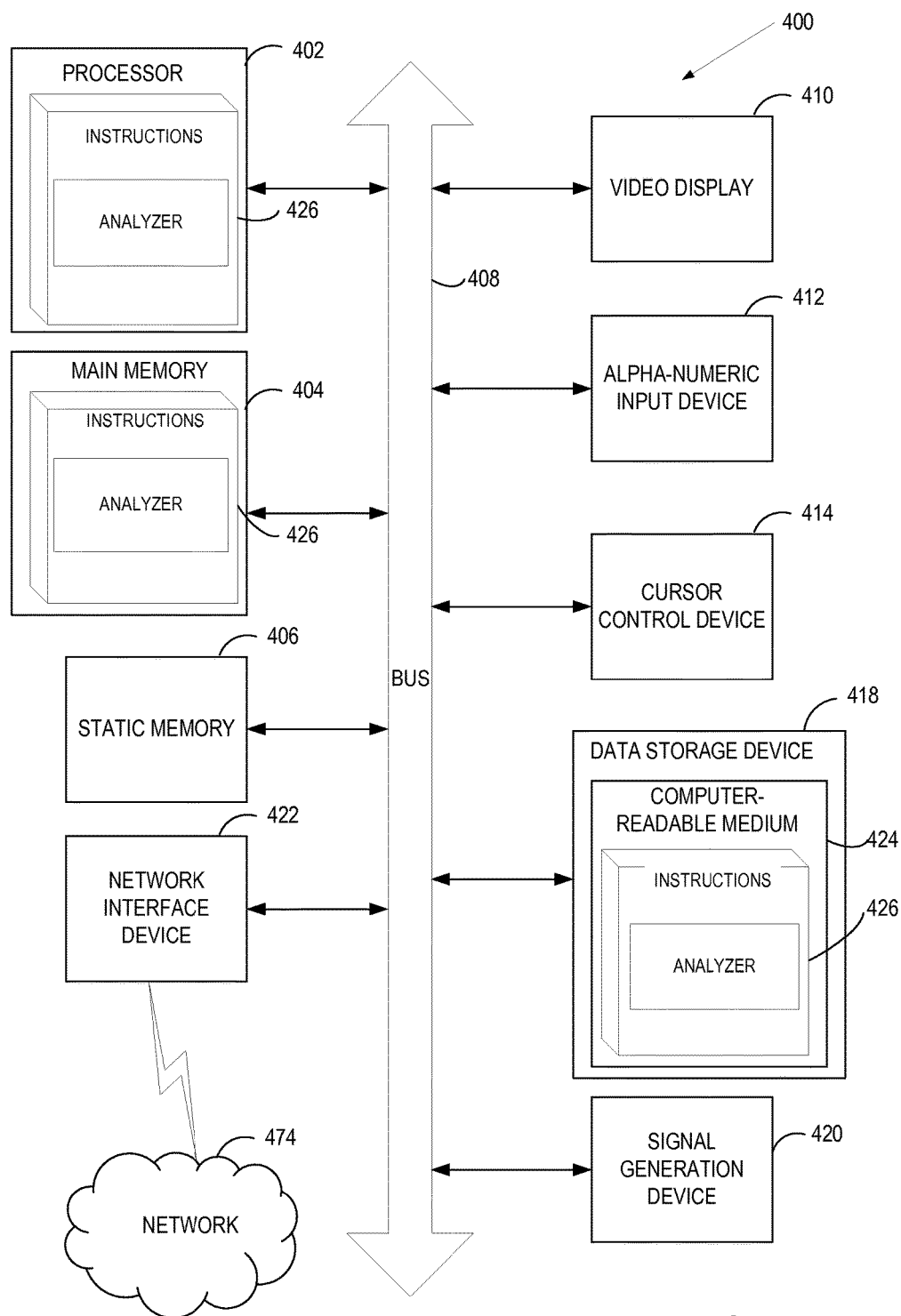
FIG. 4 is a block diagram illustrating an exemplary computer system, according to some implementations of the disclosure.

FIG. 4 illustrates a diagrammatic representation of a machine in the exemplary form of a computer system 400 within which a set of instructions, for causing the machine to perform any one or more of the methodologies discussed herein, may be executed. In alternative implementations, the machine may be connected (e.g., networked) to other machines in a LAN, an intranet, an extranet, or the Internet. The machine may operate in the capacity of a server or a client machine in client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The exemplary computer system 400 includes a processing device (processor) 402, a main memory 404 (e.g., read-only memory (ROM), flash memory, dynamic random access memory (DRAM) such as synchronous DRAM (SDRAM) or Rambus DRAM (RDRAM), etc.), a static memory 406 (e.g., flash memory, static random access memory (SRAM), etc.), and a data storage device 418, which communicate with each other via a bus 408.

Processor 402 represents one or more general-purpose processing devices such as a microprocessor, central processing unit, or the like. More particularly, the processor 402 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor 402 may also be one or more special-purpose processing devices such as an application specific integrated circuit (ASIC), a field programmable gate array (FPGA), a digital signal processor (DSP), network processor, or the like. The processor 402 is configured to execute instructions 426 for performing the operations and steps discussed herein.

The computer system 400 may further include a network interface device 422. The computer system 400 also may include a video display unit 410 (e.g., a liquid crystal display (LCD), a cathode ray tube (CRT), or a touch screen), an alphanumeric input device 412 (e.g., a keyboard), a cursor control device 414 (e.g., a mouse), and a signal generation device 420 (e.g., a speaker).

The data storage device 418 may include a computer-readable storage medium 424 on which is stored one or more sets of instructions 426 (e.g., software) embodying any one or more of the methodologies or functions described herein (e.g., instructions of the analyzer 106). The instructions 426 may also reside, completely or at least partially, within the main memory 404 and/or within the processor 402 during execution thereof by the computer system 400, the main memory 404 and the processor 402 also constituting computer-readable storage media. The instructions 426 may further be transmitted or received over a network 474 via the network interface device 422.

While the computer-readable storage medium 424 is shown in an exemplary implementation to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

In the foregoing description, numerous details are set forth. It will be apparent, however, to one of ordinary skill in the art having the benefit of this disclosure, that the present disclosure may be practiced without these specific details. In some instances, well-known structures and devices are shown in block diagram form, rather than in detail, in order to avoid obscuring the present disclosure.

Some portions of the detailed description have been presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "segmenting", "analyzing", "determining", "enabling", "identifying," "modifying" or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

The disclosure also relates to an apparatus for performing the operations herein. This apparatus may be specially constructed for the required purposes, or it may include a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an implementation" or "one implementation" or "an implementation" or "one implementation" throughout is not intended to mean the same implementation or implementation unless described as such.

Reference throughout this specification to "one implementation" or "an implementation" means that a particular feature, structure, or characteristic described in connection with the implementation is included in at least one implementation. Thus, the appearances of the phrase "in one implementation" or "in an implementation" in various places throughout this specification are not necessarily all referring to the same implementation. In addition, the term "or" is intended to mean an inclusive "or" rather than an exclusive "or."

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. A method comprising:
   receiving, by a processing device, at least one stream of data captured by at least one sensor monitoring a human subject, wherein the at least one stream of data comprises sensor measurements, and the least on sensor comprises an electroencephalography (EEG) monitor and an accelerometer integrated into headgear;
   comparing the sensor measurements to at a threshold to determine whether the human subject is in a rage state;
   determining whether to trigger an alarm based on the comparison; and
   in response to determining to trigger the alarm, generating an instruction to trigger the alarm.

2. The method of claim 1, wherein the human subject is a truck driver driving a truck.

3. The method of claim 1, further comprising:
   transmitting the instruction to trigger the alarm to an alarm receiver, wherein, in response to receiving the instruction, the alarm receiver is to generate the alarm.

4. The method of claim 3, wherein the alarm comprises at least one of a sound alarm, a flash light, a vibration, or text.

5. The method of claim 1, wherein the at least one model is built using machine learning.

6. A non-transitory machine-readable storage medium storing instructions which, when executed, cause a processing device to:
   receive, by the processing device, at least one stream of data captured by at least one sensor monitoring a human subject, wherein the at least one stream of data comprises sensor measurements, and the least on sensor comprises an electroencephalography (EEG) monitor and an accelerometer integrated into headgear;
   comparing the sensor measurements to at a threshold to determine whether the human subject is in a rage state;

determining whether to trigger an alarm based on the comparison; and in response to determining to trigger the alarm, generating an instruction to trigger the alarm.

* * * * *